United States Patent
Makuuchi et al.

(10) Patent No.: US 10,401,304 B2
(45) Date of Patent: Sep. 3, 2019

(54) EXAMINATION DEVICE

(71) Applicant: HITACHI HIGH-TECHNOLOGIES CORPORATION, Minato-ku, Tokyo (JP)

(72) Inventors: Masami Makuuchi, Tokyo (JP); Kazuma Ogawa, Tokyo (JP); Akira Hamamatsu, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 16/133,354

(22) Filed: Sep. 17, 2018

(65) Prior Publication Data

US 2019/0033228 A1    Jan. 31, 2019

Related U.S. Application Data

(63) Continuation of application No. 15/546,615, filed as application No. PCT/JP2016/052180 on Jan. 26, 2016, now Pat. No. 10,107,762.

(30) Foreign Application Priority Data

Jan. 30, 2015 (WO) .................. PCT/JP2015/052615
Mar. 16, 2015 (JP) ................................ 2015-051594

(51) Int. Cl.
| | |
|---|---|
| *G01N 21/88* | (2006.01) |
| *G01N 21/95* | (2006.01) |
| *G01N 21/94* | (2006.01) |
| *G01N 21/956* | (2006.01) |

(52) U.S. Cl.
CPC ......... *G01N 21/8806* (2013.01); *G01N 21/94* (2013.01); *G01N 21/9501* (2013.01); *G01N 21/956* (2013.01); *G01N 2021/8848* (2013.01); *G01N 2201/067* (2013.01)

(58) Field of Classification Search
CPC ........... G01N 21/8806; G01N 21/9501; G01N 21/94; G01N 2201/067; G01N 2021/8848
See application file for complete search history.

(56) References Cited

U.S. PATENT DOCUMENTS

| | | | |
|---|---|---|---|
| 4,667,256 | A | 5/1987 | Vergona |
| 7,787,114 | B2 | 8/2010 | Wolters et al. |
| 8,193,468 | B2 | 6/2012 | Cordingley et al. |
| 2005/0254065 | A1 | 11/2005 | Stokowski |

(Continued)

FOREIGN PATENT DOCUMENTS

| | | |
|---|---|---|
| JP | 47-22143 A | 7/1972 |
| JP | 50-104659 A | 8/1975 |

(Continued)

*Primary Examiner* — Sang H Nguyen
(74) *Attorney, Agent, or Firm* — Miles & Stockbridge PC

(57) ABSTRACT

The present invention provides an inspection device that is capable of detecting foreign matter with high accuracy, the inspection device including: a light source; an electro-optic element on which light from the light source is incident and which changes a phase of the light into at least two states; and a controller. The controller corrects a phase fluctuation of the electro-optic element itself, using intensity modulation characteristics of the eletro-optic element which are obtained by changing an applied voltage that is input to the electro-optic element.

3 Claims, 12 Drawing Sheets

(56) References Cited

U.S. PATENT DOCUMENTS

| | | | |
|---|---|---|---|
| 2006/0244976 A1* | 11/2006 | Baer | G01N 21/9501 356/600 |
| 2008/0304069 A1 | 12/2008 | Wolters et al. | |
| 2009/0040511 A1 | 2/2009 | Wolters et al. | |
| 2009/0201483 A1 | 8/2009 | Janssens et al. | |
| 2010/0004875 A1 | 1/2010 | Urano et al. | |
| 2010/0193481 A1 | 8/2010 | Osako | |
| 2011/0220815 A1 | 9/2011 | Sakuma et al. | |
| 2011/0298156 A1 | 12/2011 | Hooper et al. | |
| 2012/0019816 A1 | 1/2012 | Shibata et al. | |
| 2012/0092484 A1* | 4/2012 | Taniguchi | G01N 21/9501 348/87 |
| 2012/0133928 A1 | 5/2012 | Urano et al. | |
| 2013/0077086 A1 | 3/2013 | Chuang et al. | |
| 2013/0141715 A1 | 6/2013 | Urano et al. | |
| 2015/0077758 A1 | 3/2015 | Luthi et al. | |
| 2015/0192461 A1 | 7/2015 | Chen | |

FOREIGN PATENT DOCUMENTS

| | | |
|---|---|---|
| JP | 2001-144357 A | 5/2001 |
| JP | 2009-501902 A | 1/2009 |
| JP | 2009-177176 A | 8/2009 |
| JP | 2010-529461 A | 8/2010 |
| JP | 2010-190722 A | 9/2010 |

\* cited by examiner

[Fig. 1]
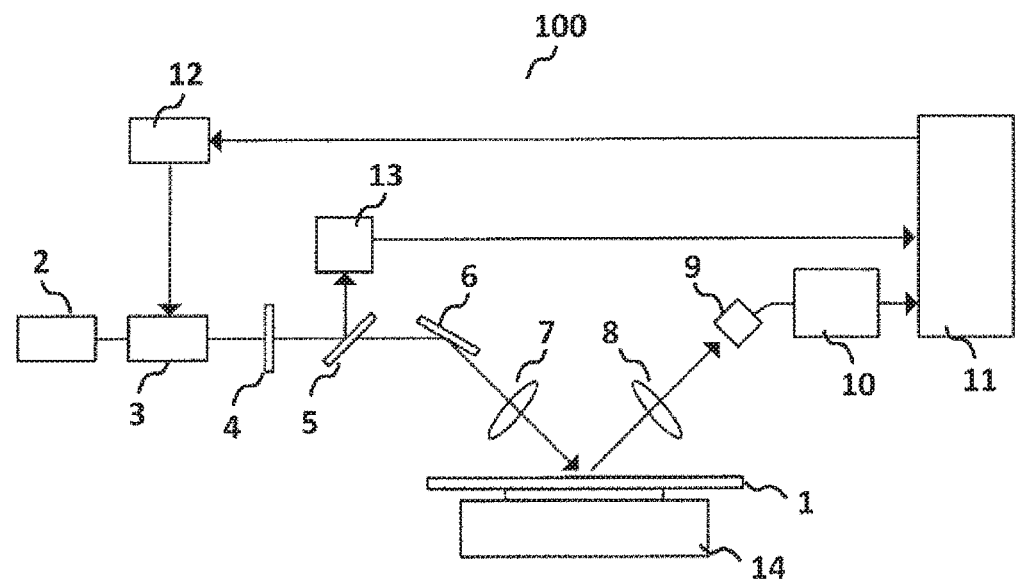
[Fig. 2]
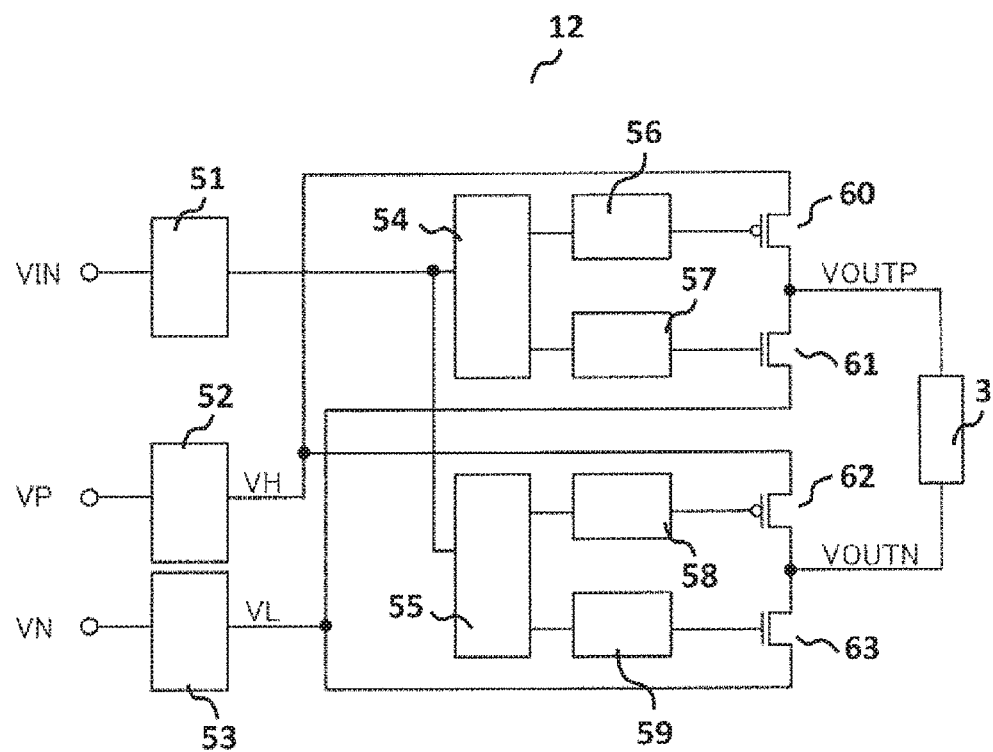

[Fig. 3]
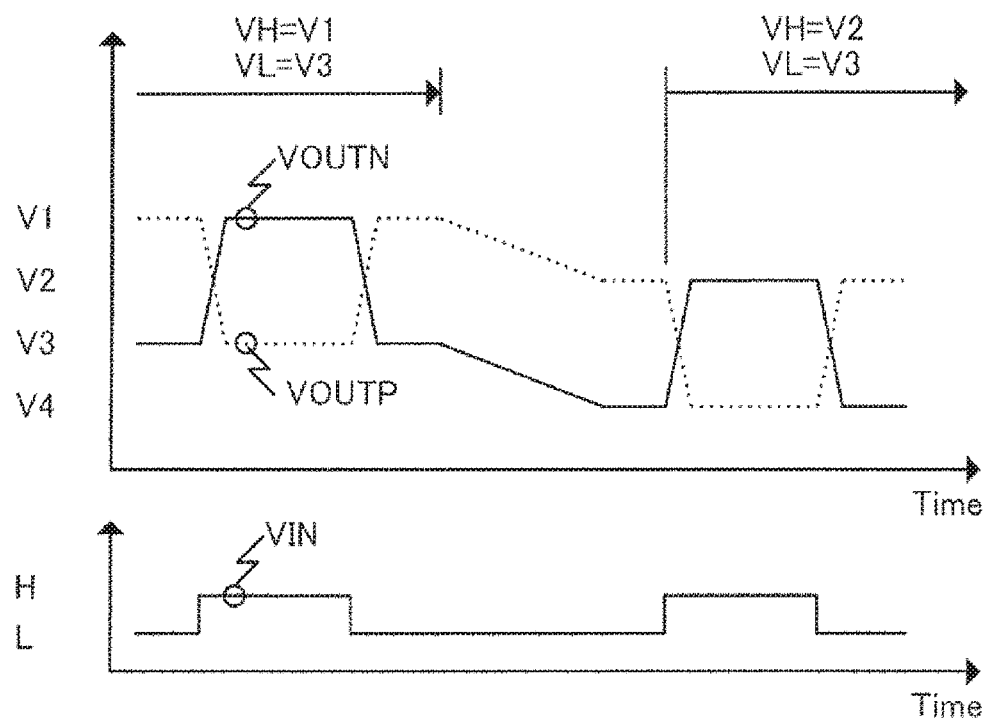

[Fig. 4]
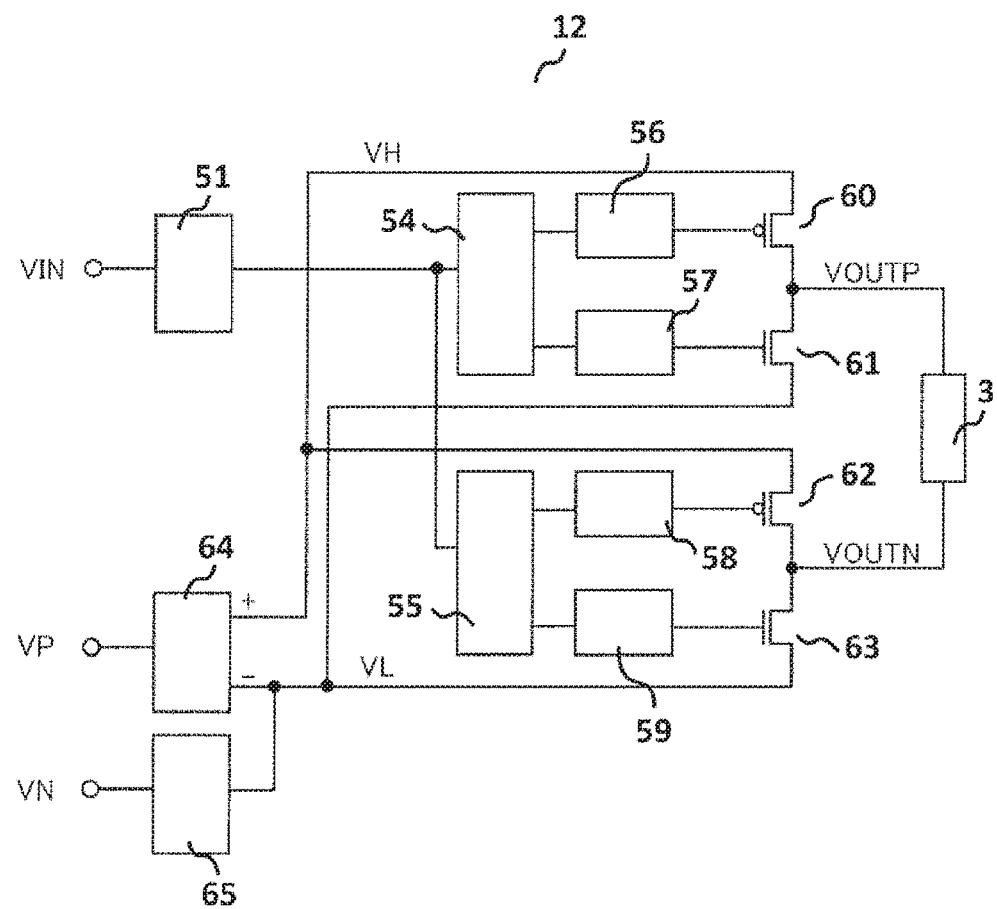

[Fig. 5]
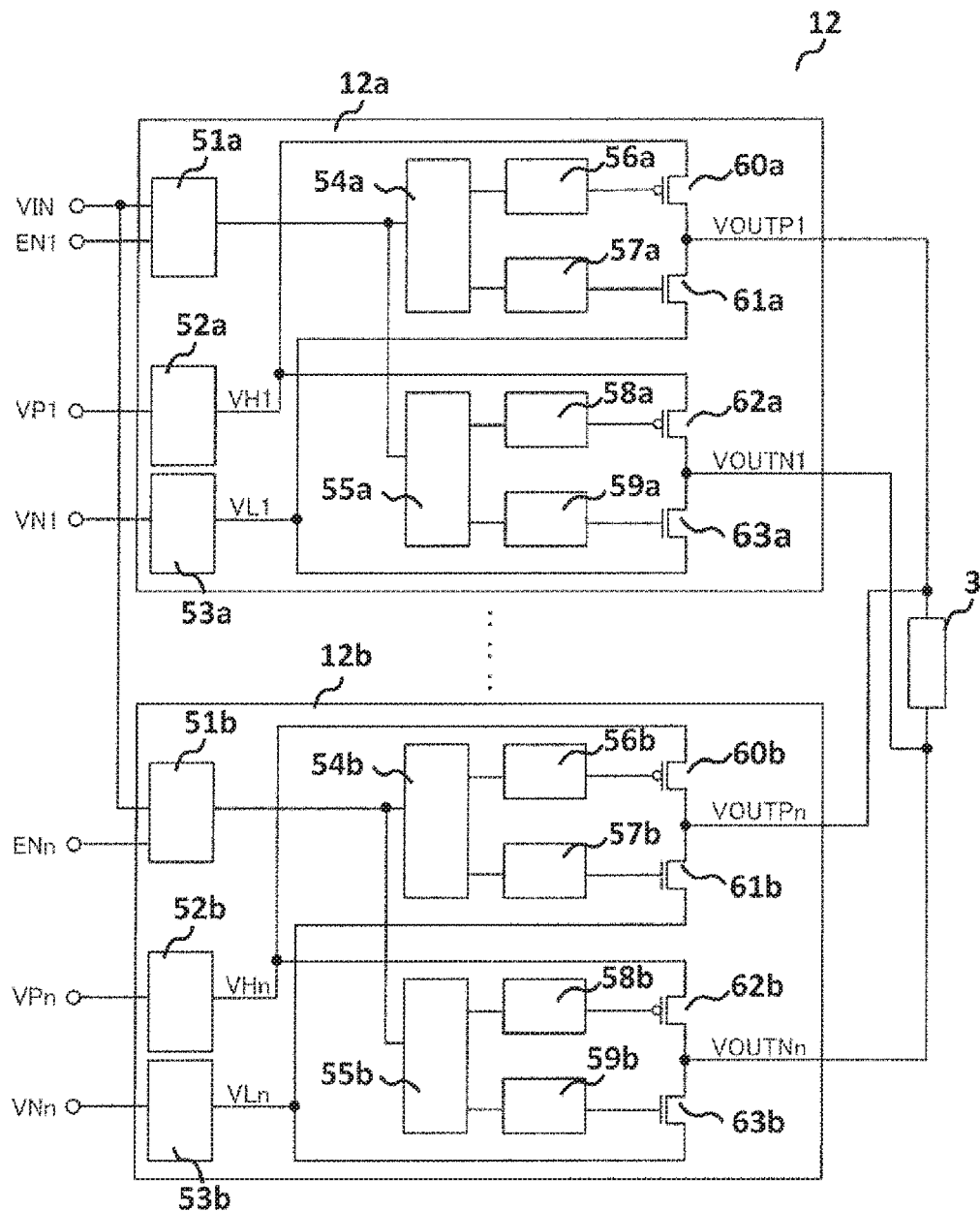

[Fig. 6]
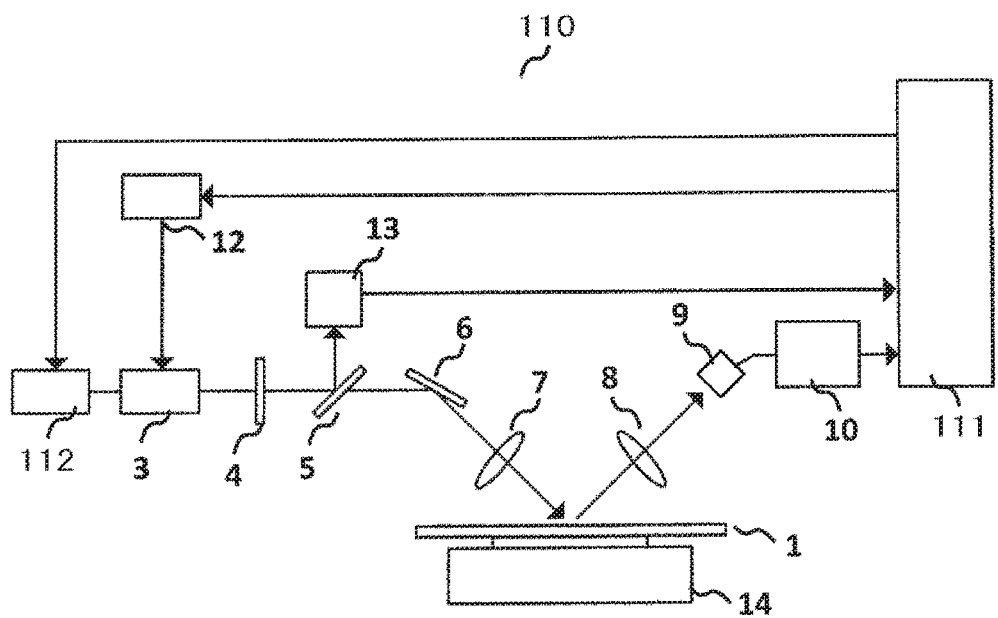

[Fig. 7]
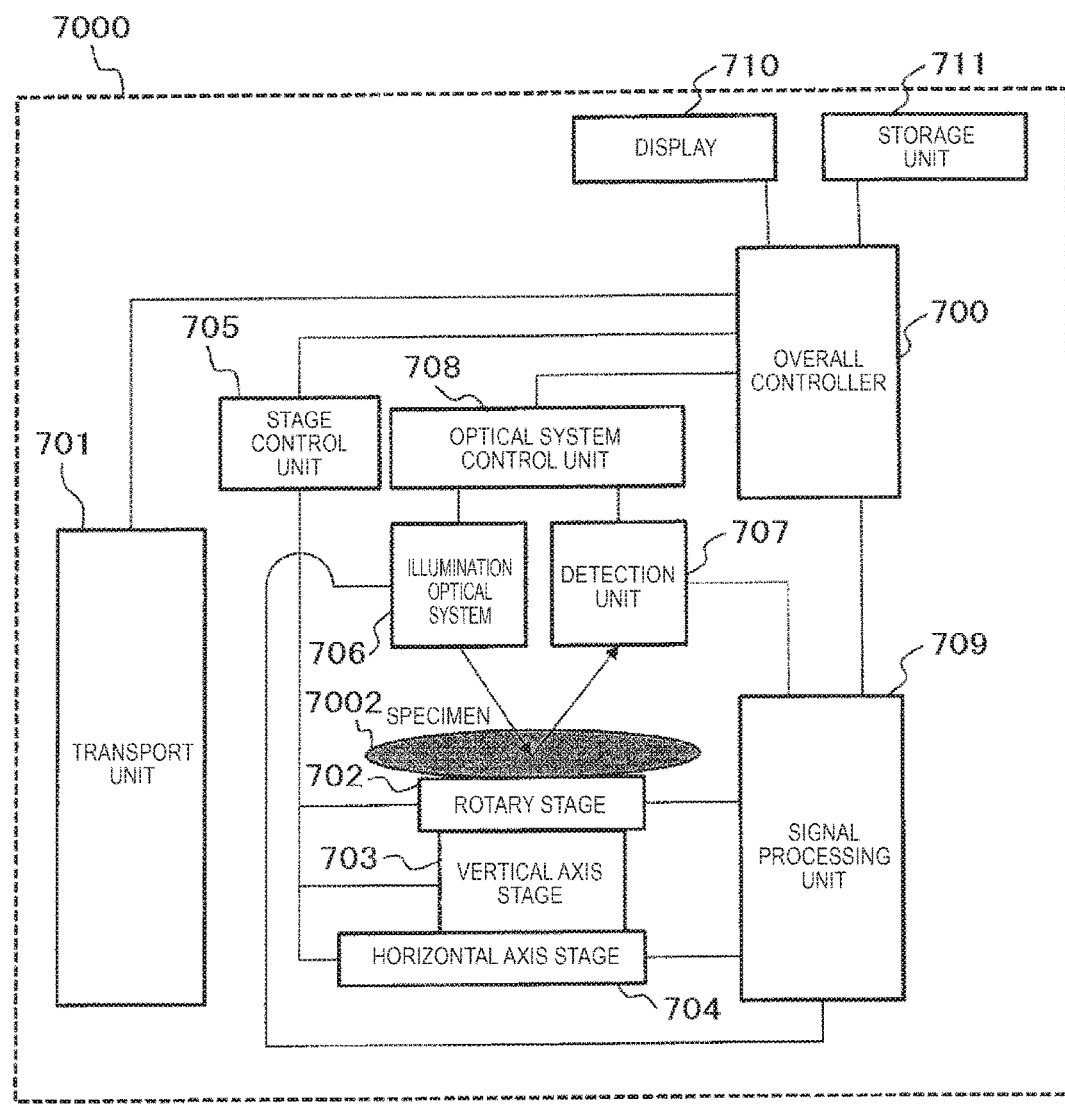

[Fig. 8]
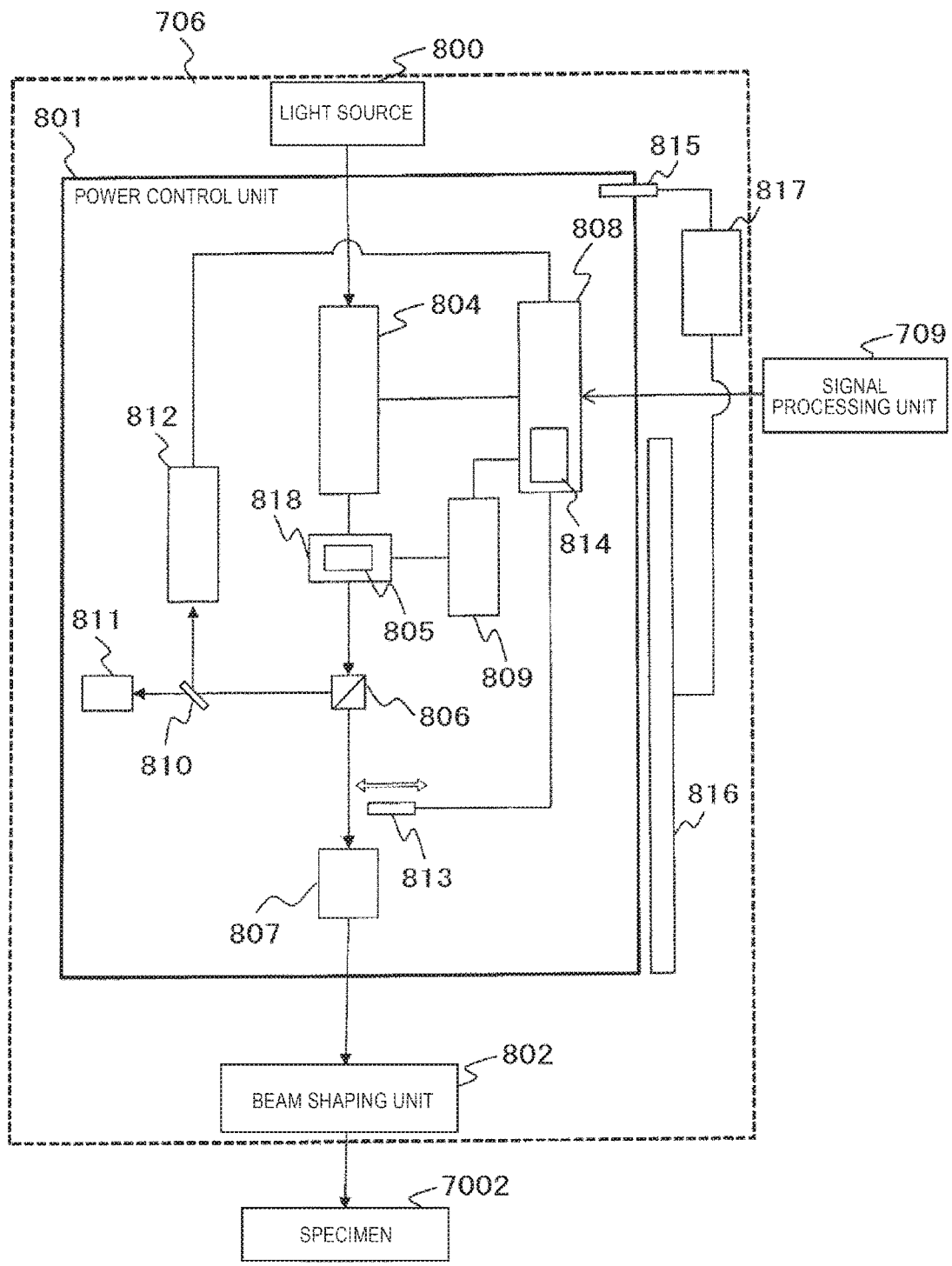

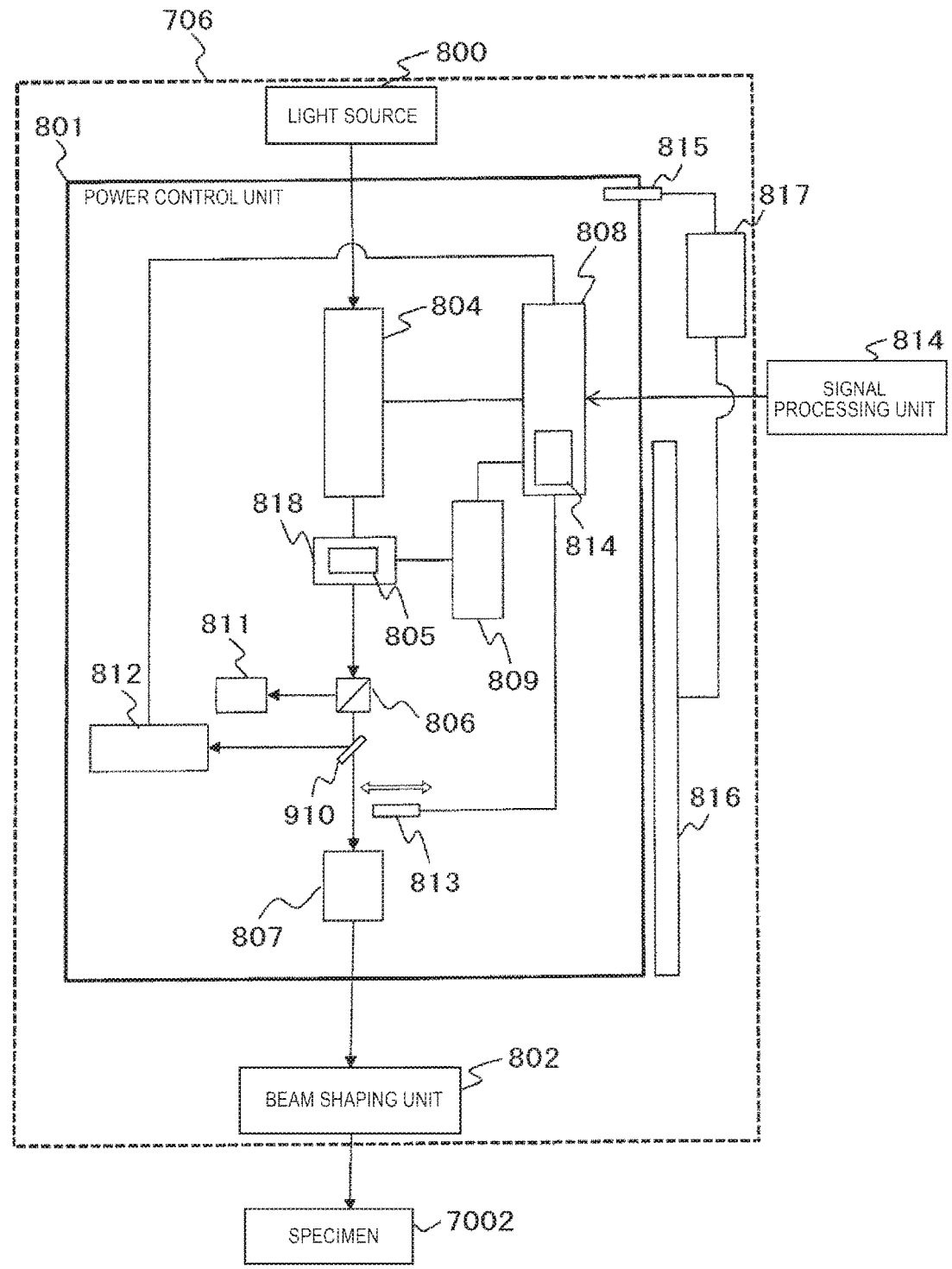
[Fig. 9]

[Fig. 10]
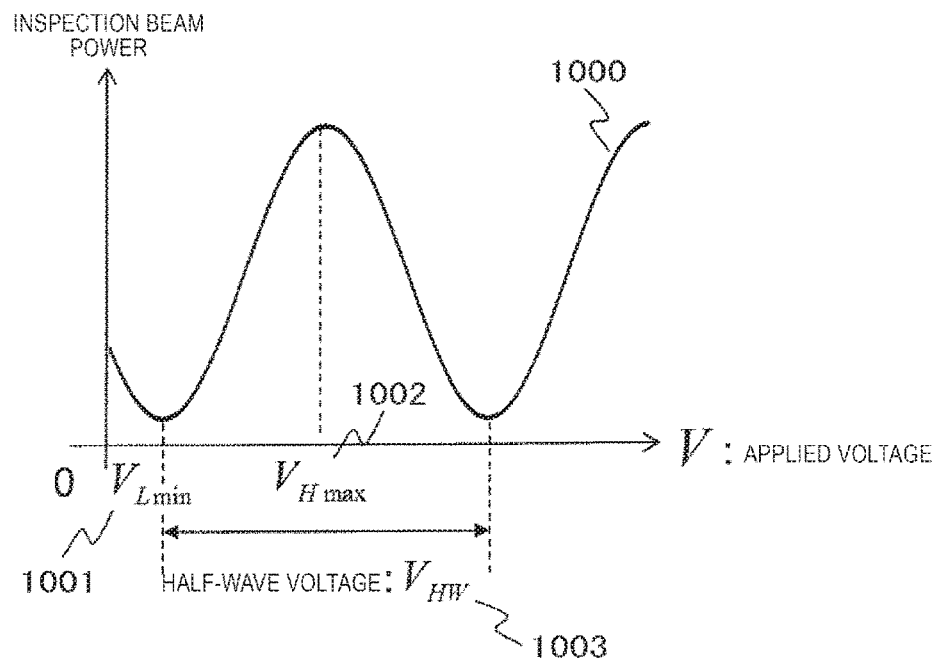
[Fig. 11]
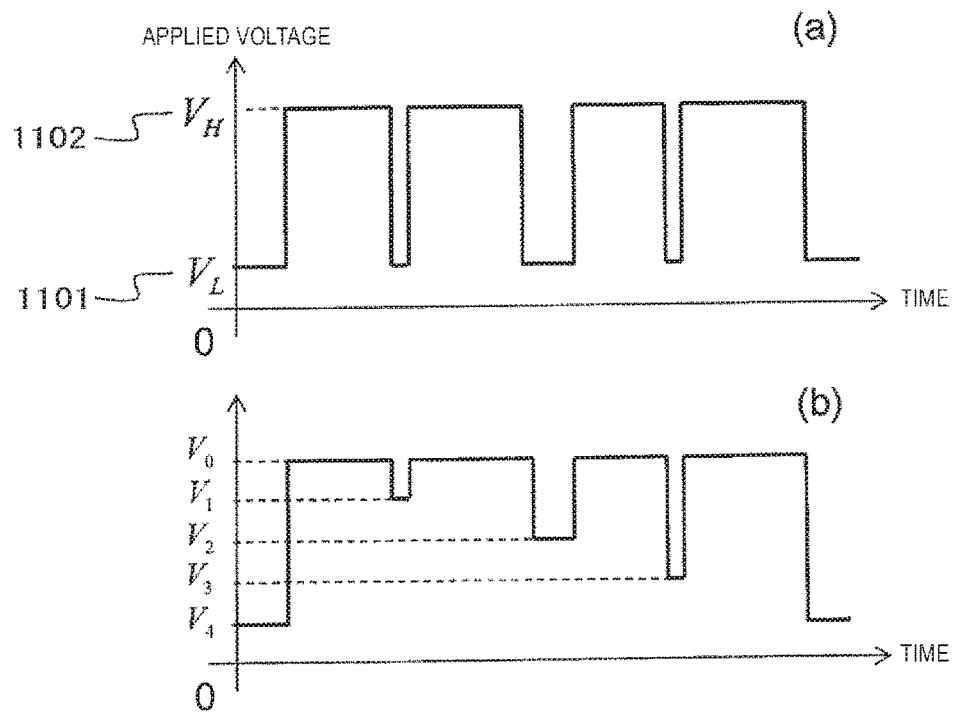

[Fig. 12]
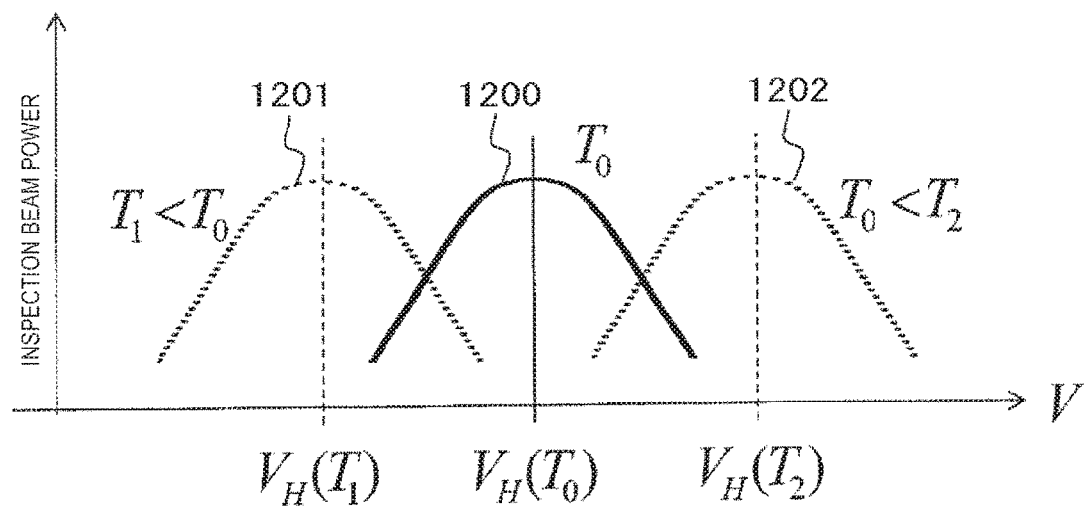

[Fig. 13]
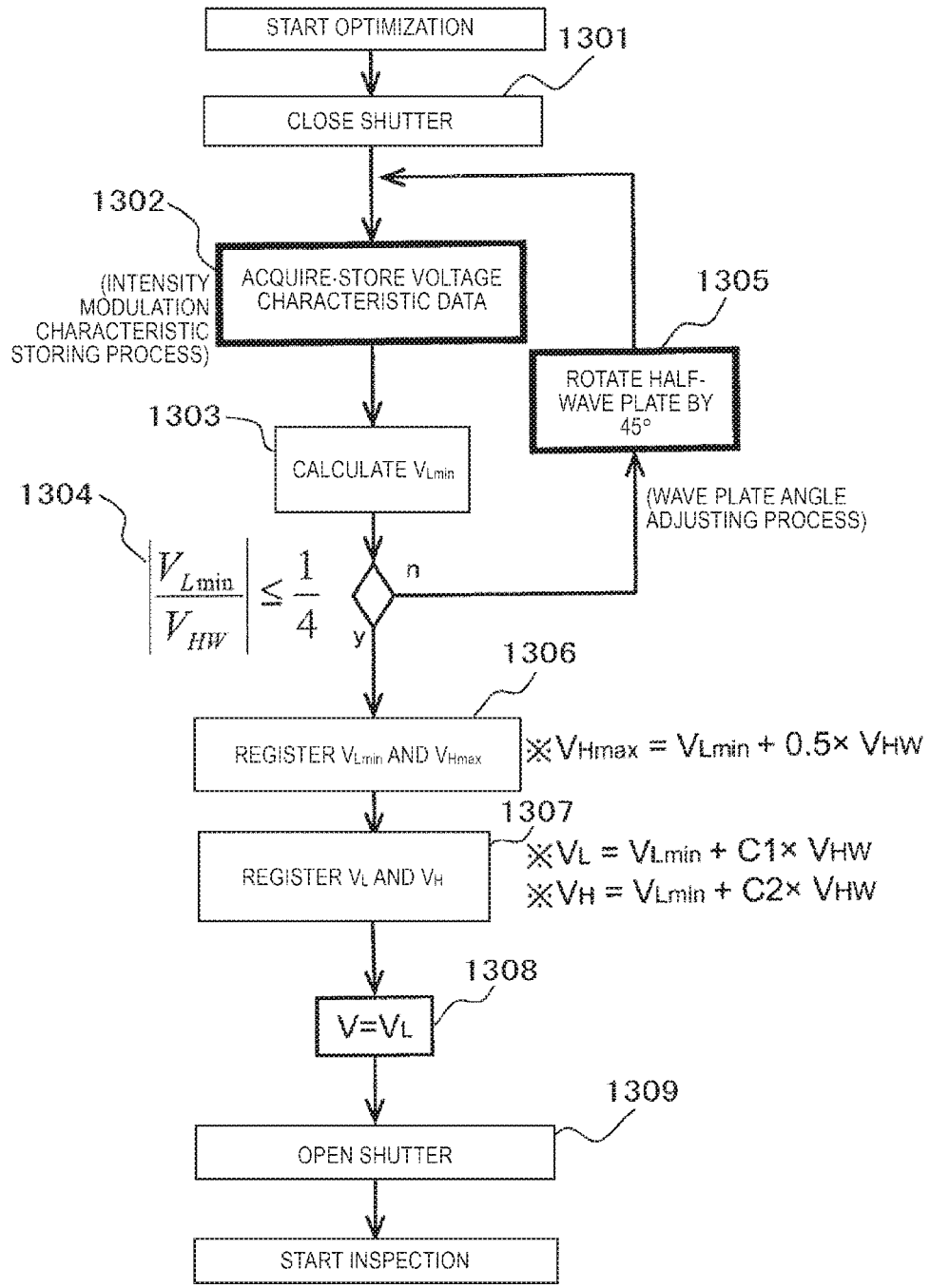

[Fig. 14]
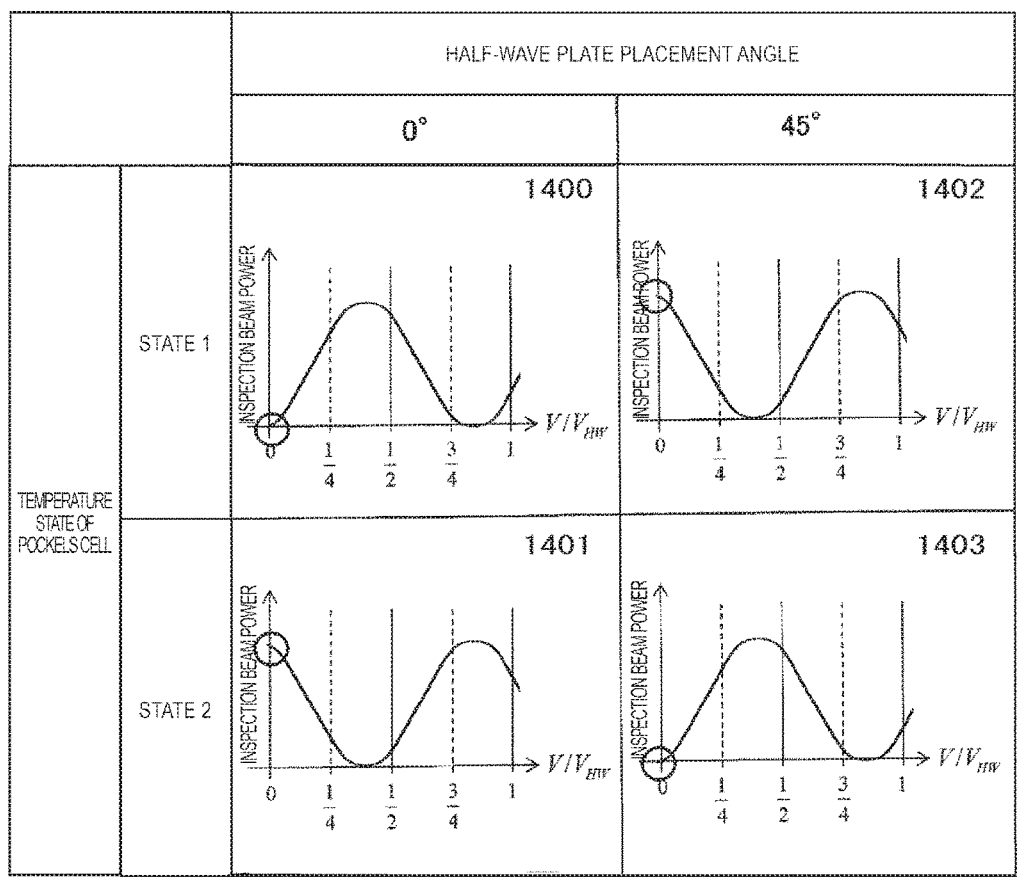

EXAMINATION DEVICE

TECHNICAL FIELD

The present invention relates to an inspection device that inspects minute foreign matter.

BACKGROUND ART

As the background art of the technical field, JP-T-2009-501902 (PTL 1) describes that "there are provided an inspection system, a circuit, and a method for enhancing flaw detection by taking measures of saturated levels of an amplifier and an analog/digital circuit as a limiting factor of a measurement detection range of an inspection system, and there are provided an inspection system, a circuit, and a method for enhancing flaw detection by reducing thermal damage to large particles due to a dynamic change in an incident laser/beam power/level at which incident laser beams are supplied to a specimen during scanning of surface inspection taking measures of saturated levels of an amplifier and an analog/digital circuit as a limiting factor of a measurement detection range of an inspection system" (see Abstract).

In addition, as described in JP-A-2001-144357 (PTL 2), means for switching and applying a predetermined voltage with respect to a Pockels cell is provided as means for driving the Pockels cell.

Further, a foreign matter inspection device for a semiconductor wafer detects a minute flaw that is present on a wafer surface, and outputs the number, a coordinate, or a size of the flaw. Due to the miniaturization of a semiconductor process, there is a demand for improvement of detection sensitivity in the foreign matter inspection device. There is a method for achieving high intensity of illumination light as an example of means for improving the detection sensitivity. However, when irradiation is performed with the illumination light having high intensity, large foreign matter having a size that exceeds hundreds of nm is broken. In this specification, this phenomenon is referred to as explosive fracture. Since fragments from the explosive fracture are spread over a specimen surface and a flawed region of the specimen is increased, an inspection power (intensity of illumination light used for inspection) needs to be limited.

In the specification of U.S. Pat. No. 7,787,114 (PTL 3), a technology of dynamically controlling an inspection power during inspection using Pockels cells is disclosed. In PTL 1, normally, while inspection is performed with high sensitivity by high-power irradiation, the inspection power is reduced during the inspection on foreign matter and the vicinity thereof such that explosive fracture is avoided in a case where there is large foreign matter.

CITATION LIST

Patent Literature

PTL 1: JP-T-2009-501902
PTL 2: JP-A-2001-144357
PTL 3: U.S. Pat. No. 7,787,114

SUMMARY OF INVENTION

Technical Problem

In a case where the inspection device for minute foreign matter operates for a long time, characteristics of a crystal change due to an influence of a laser power of a laser beam passing through the Pockels cell. Due to the characteristic change, there is a possibility that a rotating angle of a polarization plane of the laser beam passing through the Pockels cell will fluctuate and thus the laser power with which irradiation is performed on a wafer as the specimen will change. Therefore, scattered light intensity from the foreign matter on the wafer changes and thus it is difficult to detect a diameter of the foreign matter with high accuracy. However, there is no consideration of the change and detection difficulty in PTLs 1 and 2.

In addition, as PTL 3, in a case where the inspection is performed with high sensitivity due to high-power laser beam irradiation, the specimen will be irradiated with a laser beam having a high power in a case where the Pockels cell itself or a Pockels cell control unit is out of order and then abnormally stops. In the prior art, there is no consideration for the problems.

Further, since control voltage is likely to change depending on a temperature state of the Pockels cell itself, there is a possibility that it is not possible to control the laser power intended to be achieved even when a predetermined voltage is applied. In other words, the voltage characteristics of the Pockels cell itself change, and thereby there is a possibility that the specimen is likely to be irradiated with the laser beam having an excessive power which is not intended to be achieved.

The present invention provides an inspection method and an inspection device that is capable of inspecting foreign matter with high accuracy.

In addition, an object of the present invention is to safely control the laser power in an apparatus that controls the laser power by using an electro-optic element such as the Pockels cell.

Solution to Problem

In order to solve such problems described above, configurations described in claims are adopted.

The present application includes a plurality of types of means that solve the problems described above. As an example thereof, an inspection device includes: a light source; an electro-optic element on which light from the light source is incident and which changes a phase of the light into at least two states; and a controller. The controller corrects a phase fluctuation of the electro-optic element itself, using intensity modulation characteristics of the eletro-optic element which are obtained by changing an applied voltage that is input to the electro-optic element.

Advantageous Effects of Invention

According to the present invention, it is possible to detect minute foreign matter with high accuracy.

In addition, according to the present invention, even in a case where a power control system is out of order, it is possible to minimize a risk of damaging a specimen.

Problems, configurations, and effects other than the problems, configurations, and effects described above are clarified in the following description of embodiments.

BRIEF DESCRIPTION OF DRAWINGS

FIG. 1 is a block diagram showing a configuration of a foreign matter inspection device according to a first embodiment.

FIG. 2 is a block diagram showing a configuration of a driver circuit according to the first embodiment.

FIG. 3 is a graph showing an operation of the driver circuit according to the first embodiment.

FIG. 4 is a block diagram showing a configuration of a driver circuit according to a second embodiment.

FIG. 5 is a block diagram showing a configuration of a driver circuit according to a third embodiment.

FIG. 6 is an example of a block diagram showing a configuration of a foreign matter inspection device according to a fourth embodiment.

FIG. 7 is a block diagram illustrating an entire configuration of an optical inspection device according to a fifth embodiment.

FIG. 8 is a block diagram showing a configuration of an illumination optic system of the optical inspection device according to the fifth embodiment.

FIG. 9 is a block diagram showing another configuration of a power monitor system of the illumination optic system of the optical inspection device according to the fifth embodiment.

FIG. 10 is a graph illustrating a relationship (intensity modulation characteristics) between a Pockels cell applied voltage and an inspection power of the optical inspection device according to the fifth embodiment.

FIG. 11 is a graph illustrating an applied voltage to the Pockels cell of the optical inspection device according to the fifth embodiment.

FIG. 12 is a graph illustrating an influence of a temperature on voltage characteristics (intensity modulation characteristics) of Pockels cell of the optical inspection device according to the fifth embodiment.

FIG. 13 is a flowchart showing flow of a process for performing optimization of the voltage characteristics (intensity modulation characteristics) and a half-wave plate placement angle of the Pockels cell before inspection is performed by the optical inspection device according to the fifth embodiment.

FIG. 14 is a table illustrating effects of a half-wave plate in the optical inspection device according to the fifth embodiment.

DESCRIPTION OF EMBODIMENTS

The present invention relates to an inspection device that irradiates a specimen surface with a laser beam for a predetermined time and inspects a flaw on the specimen surface. The inspection device is configured to include: a laser beam source that emits a laser beam with which the specimen surface is irradiated; a modulation unit that modulates the emitted laser beam; a controller that controls a voltage which is applied to the modulation unit; and a reflected light detecting unit that detects scattered light reflected from the specimen surface and generates a detection signal. The controller performs control to switch the voltage that is applied to the modulation unit, based on a detection result obtained by the reflected light detecting unit.

In addition, an inspection device that inspects a specimen with a laser beam has an illumination optical system that includes: a laser beam source that emits a laser beam; an electro-optic element on which the laser beam from the laser beam source is incident and which changes a phase of the laser beam into at least two states; and a wave plate that rotates the phase of the laser beam. The wave plate is configured to generate a phase difference with which intensity of the laser beam, with which the specimen is irradiated in a state in which no voltage is applied to the electro-optic element, is attenuated to be lower than the maximum intensity obtained in a state in which a voltage is applied to the electro-optic element.

Hereinafter, examples will be described with reference to the figures.

Example 1

In this example, there is provided description of an example of a foreign matter inspection device that switches laser powers with which irradiation is performed on a wafer during inspection and has a stable irradiation laser power for a long time.

FIG. 1 is an example of a diagram of a configuration of the foreign matter inspection device of the example.

A foreign matter inspection device 100 includes a laser beam source 2, an optical modulation element 3, a polarization plate 4, a beam splitter 5, a mirror 6, lenses 7 and 8, a sensor 9, a detection circuit 10, a data processing unit 11, a driver circuit 12, beam power detecting means 13, and a stage 14.

In the foreign matter inspection device 100, a wafer 1 is mounted on the stage 14, and irradiation with a laser beam that is emitted from the laser beam source 2 is performed on the wafer 1 via the optical modulation element 3, the polarization plate 4, the beam splitter 5, the mirror 6, and the lens 7. At this time, in the foreign matter inspection device 100, the wafer 1 is subjected to rotational movement by the stage 14 and is subjected to linear movement by a translation stage (not illustrated), and thereby the laser beam, with which the irradiation is performed on the wafer 1, has a spiral trajectory over the entire surface of the wafer 1. Thus, it is possible to inspect the entire surface of the wafer 1. In addition, scattered light from foreign matter on the wafer 1 is detected via the lens 8, the sensor 9, and the detection circuit 10, and the data processing unit 11 performs foreign matter determination based on detection results from the detection circuit 10.

In the foreign matter inspection device 100 according to the example, the driver circuit 12 switches applied voltage to the optical modulation element 3 through switching control from the data processing unit 11. The presence or absence of foreign matter having a large diameter is predicted in the data processing unit 11, based on the detection results in a previous cycle in which scanning is performed on the wafer in a spiral shape, and the data processing unit controls the voltage switching by the driver circuit 12. Specifically, in a case where the presence of the foreign matter having a large diameter is predicted in the data processing unit 11, a laser power with which irradiation is performed on the wafer 1 is reduced.

By a predetermined voltage switched by the driver circuit 12, the optical modulation element 3 controls rotation of a polarization plane of a laser beam passing through the optical modulation element and controls the laser power of a laser beam passing through the polarization plate 4. Specifically, in a case where the presence of the foreign matter having a large diameter is predicted in the data processing unit 11, the driver circuit 12 is to output a predetermined voltage by which the laser power with which the irradiation is performed on the wafer 1 is reduced. On the other hand, in a case where the absence of the foreign matter having a large diameter is predicted, the driver circuit 12 outputs a predetermined voltage by which the laser power is increased.

In addition, in the data processing unit 11, the beam power detecting means 13 detects the laser power with which the irradiation is performed on the wafer 1 via the beam splitter 5, and a voltage value that is switched by the driver circuit 12 and is output to the optical modulation element 3 is controlled. This is because, although the optical modulation element 3 applies the same control voltage as that from the driver circuit 12, due to an environmental condition such as a temperature, a rotating angle of the polarization plane of the laser beam passing through the optical modulation element 3 is different and, as a result, the laser power with which the irradiation is performed on the wafer 1 fluctuates. Since detection accuracy of the foreign matter on the wafer 1 is degraded when the laser power fluctuates, the voltage that is switched by the driver circuit 12 is controlled such that the irradiation is performed on the wafer 1 with predetermined laser power via the beam power detecting means 13. Hence, the detection accuracy of the foreign matter is improved.

FIG. 2 is an example of a configuration of the driver circuit 12 in the foreign matter inspection device 100.

The driver circuit 12 is configured to include an input circuit 51, high-voltage generating circuits 52 and 53, level shift circuits 54 and 55, MOS drive circuits 56, 57, 58, and 59, PMOS transistors 60 and 62, and NMOS transistors 61 and 63.

In the driver circuit 12, a switching signal (VIN) from the data processing unit 11 is input to the input circuit 51 in response to the presence and absence of the foreign matter having a large diameter which is detected via the sensor 9 and the detection circuit 10, and ON/OFF control of the PMOS transistors 60 and 62 and the NMOS transistors 61 and 63 is performed from the input circuit 51 via the level shift circuits 54 and 55, and the MOS drive circuits 56, 57, 58, and 59. Further, voltages of VH and VL are generated in the high-voltage generating circuits 52 and 53 in response to voltage control signals (VP and VN) from the data processing unit 11. Here, VP represents the voltage control signal for generating the voltage of VH in the high-voltage generating circuit 52, and VN represents the voltage control signal for generating the voltage of VL in the high-voltage generating circuit 53. In addition, VH represents a voltage which is a high potential and VL represents a voltage which is a low potential from a relationship between potentials which are applied to the PMOS transistors 60 and 62 and the NMOS transistors 61 and 63.

FIG. 3 shows an example of an operation of the driver circuit 12. VIN as a switching signal is a binary signal having low and high potentials and the respective states are represented by L and H. When VIN is L, the PMOS transistor 60 turns ON from the input circuit 51 via the level shift circuit 54 and the MOS drive circuit 56, the NMOS transistor 61 turns OFF via the MOS drive circuit 57, and VOUTP is the same potential as VH.

Simultaneously, the PMOS transistor 62 turns OFF via the level shift circuit 55 and the MOS drive circuit 58, the NMOS transistor 63 turns ON via the MOS drive circuit 59, and VOUTN is the same potential as VL. As a result, a potential difference of VH−VL is applied to the optical modulation element 3.

On the other hand, when VIN is H, the PMOS transistor 60 turns OFF, the NMOS transistor 61 turns ON, and VOUTP is the same potential as VL. The PMOS transistor 62 turns ON, the NMOS transistor 63 turns OFF, and VOUTN is the same potential as VH. A potential difference of VL−VH is applied to the optical modulation element 3.

Based on the voltage control signals (VP and VN) from the data processing unit 11, generation of VH=V1 and VL=V3, or VH=V2 and VL=V4 is performed in the high-voltage generating circuits 52 and 53, respectively, and a voltage having switching amplitude: |VH−VL| and offset voltage: (VH+VL)/2 is applied to the optical modulation element 3.

Based on the detection results from the beam power detecting means 13, the switching amplitude and the offset voltage which are applied to the optical modulation element 3 via the voltage control signals (VP and VN) from the data processing unit 11 are adjusted, and thereby characteristic fluctuation of the optical modulation element 3 is corrected such that it is possible to reduce long-term laser power fluctuation with which the irradiation is performed on the wafer 1.

According to the configuration of the example, the laser power with which irradiation is performed on the wafer during inspection is switched and the long-term irradiation laser power is stabilized. In this manner, it is possible to detect the minute foreign matter with accuracy. Such effects are the same as those to be achieved in the example which will be described below.

Example 2

FIG. 4 is a diagram of a configuration showing a second embodiment of the driver circuit according to the present invention. In order to avoid complicated description, the same reference signs are assigned to the same components as those in Example 1, and thus the descriptions of the components are omitted.

The driver circuit 12 shown in FIG. 4 is configured to include the input circuit 51, high-voltage generating circuits 64 and 65, the level shift circuits 54 and 55, the MOS drive circuits 56, 57, 58, and 59, the PMOS transistors 60 and 62, and the NMOS transistors 61 and 63. The high-voltage generating circuit 64 generates a voltage in response to the voltage control signal (VP) from the data processing unit 11, and the voltage is shifted with VL generated in the high-voltage generating circuit 65 as a reference voltage. A potential difference generated in the high-voltage generating circuit 64 has the switching amplitude: |VH−VL| with respect to the optical modulation element 3. In the embodiment, the potential difference applied to the optical modulation element 3 is controlled by only the voltage control signal VP, and the offset voltage to the optical modulation element 3 is controlled by only the voltage control signal VN. In this manner, it is possible to change only one of the potential difference or the offset voltage, and a control method of the optical modulation element 3 by the data processing unit 11 is simplified.

Example 3

FIG. 5 is a diagram of a configuration showing a third embodiment of the driver circuit according to the present invention. In order to avoid complicated description, the same reference signs are assigned to the same components as those in Example 1, and thus the descriptions of the components are omitted.

The driver circuit 12 shown in FIG. 5 is configured to include a plurality of driver circuits 12a and 12b. Respective configurations of the driver circuits 12a and 12b are the same configurations as the components described in Example 1. Control signals VIN and EN1 are input to the input circuit 51 of the driver circuit 12a from the data processing unit 11, and VP1 and VN1 are input to high-voltage generating circuits 52a and 53b.

In the driver circuit 12a, predetermined voltages VH1 and VL1 are generated by the high-voltage generating circuits 52a and 53b, and control of whether or not VOUTP1 and VOUTN1 are output from EN1 is performed. In a case where EN1 can be output, VOUTP1 and VOUTN1 select and output VH1 and VL1 in response to VIN1.

Similarly, in the driver circuit 12b, output permission of VOUTPn or VOUTNn and a selection output of VHn or VLn are performed in response to the control signals VIN or ENn and VPn or VNn from the data processing unit 11. VOUTP1 and VOUTPn from the driver circuits 12a and 12b are connected to one input of the optical modulation element 3, and VOUTN1 and VOUTNn are connected to the other input thereof.

By the driver circuit 12 shown in FIG. 5, the driver circuit can select an arbitrary voltage set in advance under the control from the data processing unit 11 and can apply the voltage to the optical modulation element 3. In general, through switching of the voltages by the MOS transistors 60a to 63b rather than variable control of the voltages by the high-voltage generating circuits 52a, 53a, 52b, and 53b, it is possible to rapidly switch and control the applied voltage to the optical modulation element 3, and thus it is possible to perform the irradiation laser power control at a plurality of levels during a period of wafer inspection.

Example 4

FIG. 6 is a diagram of a configuration showing a fourth embodiment of the foreign matter inspection device according to the present invention. Similar to the above description, in order to avoid complicated description, the same reference signs are assigned to the same components as those in Example 1, and thus the descriptions of the components are omitted.

In the foreign matter inspection device 100 shown in FIG. 6, prediction of the presence and absence of the foreign matter having a large diameter is performed in the data processing unit 11, and voltage switching in the driver circuit 12 is controlled. By the predetermined voltage switched by the driver circuit 12, the rotation of the polarization plane of the laser beam passing through the optical modulation element 3 is controlled and the laser power of a laser beam passing through the polarization plate 4 is controlled. In addition, in the data processing unit 11, the beam power detecting means 13 detects the laser power with which the irradiation is performed on the wafer 1 via the beam splitter 5, and the laser power which is output with respect to the laser beam source 2 is controlled, based on the detection results.

In a case where the polarization plane of the laser beam is rotated and controlled by using only the optical modulation element 3 and the polarization plate 4, a linear relationship is not formed between a rotating angle of the polarization plane and the laser power. Therefore, in order to obtain the intended laser power with high accuracy, it is necessary to control the voltage that is applied to the optical modulation element 3 from the driver circuit 12 with high accuracy by the polarization plane of the laser beam, and the costs of the device increase.

In contrast, by combining the laser beam source 2 as described in the embodiment, there is no need to install high-cost and high-accuracy voltage generating/controlling means in the driver circuit 12, and thus it is possible to control the laser power with which the irradiation is performed on the performance wafer 1 with high accuracy.

A configuration in which the MOS transistor is used as voltage switching means is described above; however, another semiconductor switching element, a relay, or the like may be used. It is needless to say that it is possible to realize switching of the laser power with which the irradiation is performed on the wafer during the inspection and stabilization of the long-term irradiation laser power under switching control with respect to the elements and dynamic control of a power supply voltage which is a connection source.

In addition, switching of the voltages of two values as VH and VL is described above; however, as described in Example 3, it is needless to say that it is possible to realize the control of the irradiation laser power at a plurality of levels by switching the plurality of voltages with driver circuits arranged.

The present invention is not limited to the examples described above, and includes various modification examples.

For example, the examples are described in detail for easy understanding of the present invention, and the present invention is not necessarily limited to inclusion of the entire configurations described above. In addition, it is possible to replace a part of a configuration of an example with a configuration of another example, and it is possible to add a configuration of an example to a configuration of another example. In addition, it is possible to add another configuration to, to remove, or to replace, with another configuration, a part of each of the configurations of the examples. Specific modification examples are as follows.

As Modification Example 1, there is provided a flaw inspection device that irradiates a specimen surface with a laser beam for a predetermined time and inspects a flaw on the specimen surface. The flaw inspection device includes: a laser beam source that emits a laser beam with which the specimen surface is irradiated; a modulation unit that modulates the emitted laser beam; a controller that controls a voltage which is applied to the modulation unit; and a reflected light detecting unit that detects scattered light reflected from the specimen surface and generates a detection signal. The controller performs control to switch the voltage that is applied to the modulation unit, based on a detection result obtained by the reflected light detecting unit.

As Modification Example 2, there is provided a flaw inspection device that irradiates a specimen surface with a laser beam for a predetermined time and inspects a flaw on the specimen surface. The flaw inspection device includes: a laser beam source that emits a laser beam with which the specimen surface is irradiated; a modulation unit that modulates the emitted laser beam; a controller that controls a voltage which is applied to the modulation unit; and a laser power detecting unit that detects laser power which is modulated and with which the irradiation is performed on the specimen surface. The controller controls the voltage that is applied to the modulation unit in a case where laser power obtained at first time and power obtained at second time are different from each other as a result of the detection by the laser power detecting unit at the first time and the second time.

As Modification Example 3, there is provided a flaw inspection device described in Modification Examples 1, the flaw inspection device including: a laser power detecting unit that detects the laser power which is modulated and with which the irradiation is performed on the specimen surface. The controller controls the voltage that is applied to the modulation unit in a case where the laser power obtained at first time and the power obtained at second time are different from each other as a result of the detection by the laser power detecting unit at the first time and the second time.

As Modification Example 4, there is provided a flaw inspection device described in Modification Example 2 or 3, in which the controller includes a first voltage generating unit that generates a first voltage which is applied to the modulation unit, based on a result detected by the laser power detecting unit, a second voltage generating unit that generates a second voltage, and a voltage switching unit that switches the generated first voltage or the generated second voltage and applies the voltage to the modulation unit. The controller performs variable control of the voltages that are generated by the first voltage generating unit and the second voltage generating unit.

As Modification Example 5, there is provided a flaw inspection device described in any one of Modification Examples 1 to 3, in which the controller has the first voltage generating unit and the second voltage generating unit and applies, to the modulation means, a potential difference between the first voltage generating unit and the second voltage generating unit.

As Modification Example 6, there is provided a flaw inspection device described in any one of Modification Examples 1 to 3, the flaw inspection device further including the plurality of the controllers.

As Modification Example 7, there is provided a flaw inspection device described in any one of Modification Example 2 or 3, in which the controller controls the laser power of a laser beam that is emitted from the laser beam source, based on a detection result obtained by the laser power detecting unit.

As Modification Example 8, there is provided a flaw inspection method in which a specimen surface is irradiated with a laser beam for a predetermined time and a flaw is inspected on the specimen surface. The flaw inspection method includes: a laser beam emitting step of emitting a laser beam with which the specimen surface is irradiated; a modulating step of applying a voltage and modulating the emitted laser beam; a control step of controlling the voltage that is applied in the modulating step; and a reflected light detecting step of detecting scattered light reflected from the specimen surface and generating a detection signal. In the control step, the voltage that is applied in the modulating step is switched, based on a detection result obtained in the reflected light detecting step.

As Modification Example 9, there is provided a flaw inspection method described in Modification Example 8, the flaw inspection method further including: a laser power detecting step of detecting the laser power which is modulated and with which the irradiation is performed on the specimen surface. In the control step, the voltage that is applied in the modulating step is controlled in a case where the laser power obtained at first time and the power obtained at second time are different from each other as a result of the detection in the laser power detecting step at the first time and the second time.

As Modification Example 10, there is provided a flaw inspection method described in Modification Example 9, in which the control step includes a first voltage generating step of generating a first voltage which is applied to the modulating step, based on a result detected in the laser power detecting step, a second voltage generating step of generating a second voltage, and a voltage switching step of switching the generated first voltage or the generated second voltage and applying the voltage in the modulating step. In the control step, it is possible to perform variable control of the voltages that are generated in the first voltage generating step and the second voltage generating step.

As Modification Example 11, there is provided a flaw inspection method described in Modification Example 8 or 9, in which the control means has the first voltage generating step and the second voltage generating step and applies a potential difference between potentials obtained in the first voltage generating step and the second voltage generating step.

As Modification Example 12, there is provided a flaw inspection method described in Modification Example 9, in the control step, the laser power of a laser beam that is emitted in the laser emitting step is controlled, based on a detection result obtained in the laser power detecting step.

In addition, control wires or information wires are illustrated when the wires are considered to be necessary for description, and all of the control wires or the information wires are not necessarily illustrated for a product. Actually, almost all of the configurations may be considered to be connected to each other.

Example 5

Hereinafter, as Example 5, an example in which a semiconductor inspection device using an optical inspection device is described; however, the example is only an example of the present invention, and the present invention is not limited to an embodiment which will be described below. In the present invention, the optical inspection device includes a wide range of devices using a laser beam. Hereinafter, examples of the optical inspection device include a system to which the optical inspection device is connected via a network and a combined device of a charged particle beam device, and the devices are collectively referred to as an optical inspection system.

In the example, examples of the "specimen" include a semiconductor wafer having a fine pattern, a wafer before the pattern is formed, a photomask (exposure mask), a liquid crystal substrate, or the like.

FIG. 7 is a diagram illustrating a schematic configuration of an optical inspection device 1 as an example of the semiconductor inspection device to which the present invention is applied. An optical inspection device 7000 is configured to include a transport system, a stage system, an optical system, and a data processing system, and the systems are controlled by an overall controller 100.

A specimen 7002 is carried to a stage in an inspection chamber by a transport unit 701 that includes a robotic arm therein and is adjacent to the inspection chamber and the specimen is fixed to the stage by vacuum suction or an edge clip.

A specimen stage is configured to have a rotary stage 702, a vertical axis stage 703, and a horizontal axis stage 704, and a stage control unit 705 controls the stages. The vertical axis stage 703 causes focus surfaces of an illumination optical system 706 and a detection unit 707 to be coincident with the specimen surface, by using a distance sensor (not illustrated) fixed to a reference surface of the illumination optical system 706. The stage is moved in a radial direction while being rotated, and thereby it is possible to inspect the entire surface of the specimen.

An optical system is configured to include the illumination optical system 706 and the detection unit 707. The illumination optical system 706 is configured to include a laser beam source, a lens, and an aperture, and will be described in detail with reference to FIGS. 8 and 9. The illumination optical system 706 modulates an illumination beam to an appropriate power, the illumination beam is shaped to have an appropriate spot size, and illuminates the specimen 7002. The detection unit 707 is configured to include a detector and a detection optical system having a plurality of lenses, concentrates the scattered light from the specimen 7002 on the detector, and converts the detection result into an electrical signal to transmit the signal to a signal processing unit 709. The optical system control unit 708 controls the illumination optical system 706 and the detection unit 707, and arrangement of optical elements and a gain of the detector are adjusted depending on inspection conditions.

The signal processing unit 709 appropriately processes a signal input from the detection unit 707 and performs flaw determination. At this time, a size of a flaw is determined, based on the intensity of the signal. In addition, a coordinate of the flaw is determined, by using an encoder signal input from the rotary stage 702 and the horizontal axis stage 704.

Data processed in the signal processing unit 709 is transmitted to an overall controller 700, and is displayed on a display 710 or is stored in a storage unit 711 as a data file.

A configuration of the system is not limited thereto, and a part or the entirety of a device constituting the system may be a common device.

The overall controller 700, the stage control unit 705, the optical system control unit 708, and the signal processing unit 709 can be realized in any type of hardware or software. In a case of a configuration as the hardware, the units can be realized by integrating a plurality of computing elements that execute processes on a wiring board, or in a semiconductor chip or a package. In a case of a configuration as the software, the units can be realized by causing a central processing unit (CPU) mounted on the device constituting the system or a general-purpose CPU mounted on a general-purpose computer connected to the system to execute a program for executing a desired arithmetic processing.

FIG. 8 shows an example of a configuration of the illumination optical system 706. The illumination optical system is configured to include a light source 800, a power control unit 801, and a beam shaping unit 802.

For example, a laser beam source is used as the light source 800. In order to detect a minute flaw in the vicinity of the specimen surface, an ultraviolet or vacuum ultraviolet laser beam having a short wavelength is oscillated and a high power light source having a power of 1 W or higher is used.

The beam shaping unit 802 is an optical unit that forms a predetermined illumination shape and is configured to include a beam expander, for example.

The power control unit 801 is mainly configured to include a Pockels cell 804, a half-wave plate 805, a polarization beam splitter 806, and an attenuator (static attenuator) 807. Hereinafter, an example in which the Pockels cell is used as an example of the electro-optic element will be described; however, an element of which a polarization direction of beam is electrically switched may be used. The laser beam incident on the Pockels cell 804 is subjected to phase modulation depending on an applied voltage from a Pockels cell control unit 808. Further, a certain amount of the laser beam is subjected to the phase modulation by the half-wave plate 805 disposed at the back of the Pockels cell and is incident on the polarization beam splitter 806. Here, it is important that the half-wave plate 805 is in front of the polarization beam splitter. The half-wave plate 805 is fixed to the rotary stage 818 and can be placed at any angle. A half-wave plate control unit 809 controls a placement angle. The placement angle used in the example is two types of 00 and 45° and, in order to obtain a phase modulation effect of the two types of placement angles, the 45°-placed half-wave plate may be configured to be loaded and unloaded on an optical path by a directly moving stage.

The beam subjected to the phase modulation by the Pockels cell 804 and the half-wave plate 805 diverges into two optical paths by the polarization beam splitter 806. The beam transmitted through the polarization beam splitter 806 is referred to as the inspection beam and the reflected beam is referred to as non-inspection beam. It is possible to adjust a ratio of the inspection beam and the non-inspection beam by the Pockels cell applied voltage and the placement angle of the half-wave plate.

The non-inspection beam is transmitted through a beam sampler 810 and is incident on a diffuser 811. Here, an element having an amount of the reflected beam which is larger than an amount of the transmission beam is used as the beam sampler 810. A part of beam reflected from the beam sampler 810 is caused to be incident on a power monitor 812 and a power level is always monitored.

A power monitor signal is input to the Pockels cell control unit 808 and is used to detect abnormality of the Pockels cell, and to optimize the Pockels cell applied voltage.

In a case where a control signal and the power monitor signal are compared to each other in the Pockels cell control unit 808 and a power that is not coincident with the control signal is detected, an interlock circuit that closes an optical path shutter 813 is used.

The optical path shutter 813 is disposed at the back of the polarization beam splitter 806 that forms divergence to the power monitor 812, and thereby it is possible to check that correct control is performed before the specimen 7002 is illumined.

Further, the maximum value of the illumination power is limited by the attenuator 807 at the final end of the power control unit, and it is possible to limit the irradiation power to the specimen and a fail-safe is realized even in a case where it is not possible to control the intensity modulation by the Pockels cell.

Since the Pockels cell 804 has characteristics that change depending on the temperature, a thermometer 815 and a heater 816 are provided in the power control unit 201, and a temperature control unit 817 controls the temperature to be a constant temperature. A cooler may be used instead of the heater 816, or a unit having a function of performing both of the heating and cooling may be used.

As described above, it is possible to take measures of constant temperature control with respect to a relatively long-term temperature fluctuation, and it is effective to improve reliability of the performance of the inspection device.

FIG. 9 shows another example of a configuration of the illumination optical system 706. The configuration differs from that in FIG. 8 in that a beam sampler 910 is disposed on the optical path of the inspection beam and a part of the inspection beam is monitored by the power monitor 812. Here, an element having an amount of the reflected beam which is larger than an amount of the transmission beam is used as the beam splitter 910. In this case, the optical path shutter 813 is disposed at the back of the beam sampler 810. According to the configuration in FIG. 9, unlike the configuration in FIG. 8, since the inspection beam itself diverges and is monitored, it is possible to more directly check the state of the inspection beam.

Next, the power modulation using the Pockels cell is described with reference to the figures.

FIG. 10 shows a relationship (intensity modulation characteristics) between the Pockels cell applied voltage and the inspection power. When a voltage is applied to the Pockels cell, a polarization axis is rotated with respect to a transmission axis of the polarization beam splitter 806, and thus voltage characteristics (intensity modulation characteristics) 1000 as shown in FIG. 10 are obtained. When a voltage VLmin1001 is applied, the polarization axis is rotated by 90° with respect to the transmission axis of the polarization beam splitter 806 and the minimum inspection beam power is obtained. When a voltage VHmax1002 is applied, the polarization axis is coincident with the transmission axis of the polarization beam splitter 806 and the maximum inspection beam power is obtained. A voltage obtained when the polarization axis is rotated by 180° is referred to as a half-wave voltage VHW1003 and is an index of the voltage characteristics of the Pockels cell.

FIG. 11(*a*) shows an example of the Pockels cell applied voltage. The Pockels cell applied voltage has a first level VL1101 and a second level VH1102 as references. The Pockels cell control unit can arbitrarily designate the levels. For example, when the first level is set to the voltage VLmin at which the minimum inspection power is obtained, and the second level is set to the voltage VHmax at which the maximum inspection beam power is obtained, the applied voltage is switched to VLmin and VHmax, and thereby it is possible to switch between the minimum power and the maximum power. A ratio of the minimum power and the maximum power is determined by an extinction ratio of the Pockels cell and, in general, 1:50 to 1:1000. In a case where the Pockels cell having the extinction ratio of 1:50 is used, it is possible to perform switching to a power of 2% of the maximum power when the maximum power is 100%.

In addition, when a plurality of levels are set between VLmin and VHmax as shown in FIG. 11(*b*), it is possible to obtain any power between 2% to 100%.

For example, in a case where large foreign matter is present on the specimen surface and a position thereof is found in advance using any methods, switching to a control voltage is performed in the vicinity of the large foreign matter and the inspection power is reduced. Hence, while the explosive fracture of the large foreign matter is suppressed, it is possible to increase the inspection power in the other region and to inspect the region with high sensitivity. Examples of a method of finding the large foreign matter in advance are considered to include a method of performing pre-inspection before the main inspection, a previous detection method using an end portion of the inspection light beam, or the like.

The phase modulation effects of the Pockels cell are changed due to not only the applied voltage, but also the temperature. FIG. 12 shows an example in which the voltage characteristics of the Pockels cell are changed due to the temperature. The voltage characteristics 1200 at a certain reference temperature (T=T0) are changed to 1201 due to a temperature drop (T=T1) and are changed to 1202 due to a temperature rise (T=T2). In other words, the voltage, by which the maximum power of the inspection beam is obtained, is changed. It is necessary to control the temperature around the Peckels cell such that the temperature is constant; however, the temperature control is performed with low accuracy and a reaction rate is also delayed. Hence, it is preferable that correction of the influence of a relatively short-term temperature fluctuation is performed by the applied voltage.

FIG. 13 is a flowchart illustrating voltage correction flow. In order to first prevent erroneous irradiation before an inspection start, an optical path shutter 813 is closed (Step 1301). In order to acquire voltage characteristics as shown in FIG. 10, the applied voltage to the Pockels cell is changed in a certain range and pitch such that data of non-inspection beam power is acquired, and the data is stored in the intensity modulation characteristic storage unit 814 in FIGS. 8 and 9 (an intensity modulation characteristic storing process in Step 1302). VLmin is obtained from the acquired voltage characteristic data (Step 1305). In a case where whether the value of the obtained VLmin satisfies conditional Expression 1304 is checked and the value does not satisfy the expression, the placement angle of the half-wave plate is changed (a wave plate angle adjusting process in Step 1305). Here, Conditional Expression 1304 represents a condition for suppressing the inspection beam power obtained in a state in which the applied voltage is 0 to be equal to or lower than 50% of the maximum power obtained in a state in which the voltage is applied (FIG. 8 showing a reason why it is possible to suppress the power to be equal to or lower than 50%). When VLmin that satisfies Conditional Expression 1304 is determined, and VHmax is calculated from VLmin and is registered as a constant representing the voltage characteristics of the Pockels cell (Step 1306). Here, a calculation expression depends on FIG. 10. VL and VH that are actually used as the control voltage are obtained from VLmin and VHmax and are registered (Step 1307). Here, fixed values 1 and 2 used when VL and VH are obtained are constants that are determined, depending on levels of the maximum power and the minimum power.

Finally, VL is set as the voltage value obtained at the time of inspection start (Step 1308). After a stable state is set, the shutter is opened (Step 1309) and the inspection is started.

In other words, the voltage correction flow shown in FIG. 13, particularly, the intensity modulation characteristic storing process (Step 1302) is always executed before the inspection, and thereby it is possible to repeat and store the influence of the relatively short-term temperature fluctuation as a type of fluctuation of the voltage characteristics of the Pockels cell. Therefore, the voltage is applied to the Pockels cell at the time of the inspection, based on the stored intensity modulation characteristics, and it is possible to correct the influence of the temperature fluctuation.

Here, an expression, during the inspection, means that it is the time in the middle of execution of the inspection on the specimen 7002 which is performed by illuminating the laser beam of the illumination optical system 706 on the specimen 7002, receiving the scattered light from the specimen 7002 by the detection unit 707, and then performing the flaw determination in the signal processing unit 709. In addition, an expression, before the inspection, means that it is the time before the inspection is performed, that is, it is the time including not only immediately after the specimen 7002 is transported into the inspection chamber, but also before the next predetermined inspection is performed after a predetermined inspection is ended.

A table in FIG. 14 is to show that it is possible to suppress the inspection power obtained in a case where the applied voltage is 0 to be equal to or lower than 50% of the maximum power obtained in a state in which the voltage is normally applied by the rotary wave plate (a wave plate angle adjusting process). The horizontal axis represents a value obtained by normalizing the applied voltage into a half-wave voltage, and the vertical axis represents the inspection beam power. A state 1 and a state 2 represent different temperature states from each other.

In the state 1, in a case (1400) where the half-wave plate placement angle is 0°, the transmission power is lower than 50% even when it is not possible to apply the voltage during the inspection (that is, V=0). However, in the state 2, in a case 1401 where the half-wave plate placement angle is 0°, the transmission power is higher than 50% at the moment when the application of voltage is stopped. In a case of the state of 1401 in which the optimization is performed before the inspection, Conditional Expression 1304 in FIG. 13 is not satisfied, and thus the half-wave plate is rotated. Then, since the state of 1401 is switched to a state of 1403, the inspection power is lower than 50% in a state in which it is not possible to perform the voltage control. Similarly, since a state of 1402 does not satisfy Conditional Expression 1304, the half-wave plate is rotated and the state is switched to the state of 1400. In other words, the half-wave plate is placed at 0° such that the characteristics as in 1400 are obtained when the temperature is in the state 1, and the half-wave plate is placed at 45° such that the characteristics as in 1403 are obtained when the temperature is in the state 2. In other words, an offset is applied to a phase on the wave plate such that the power of the minimum inspection beam (preferably, 0) is obtained when the applied voltage to the Pockels cell is 0.

According to the example, even in a case where any type of abnormality occurs in the Pockels cell itself or the Pockels cell control unit, and the voltage is not applied, it is possible to limit the transmission power to be equal to or lower than 50% of the maximum power in a state in which the voltage is applied. In this manner, it is possible to minimize a risk of damaging the specimen 7002.

In addition to this, it is possible to correct the influence of the relatively short-term temperature fluctuation to the extent that the temperature changes for each time of the inspection by the voltage characteristic data acquisition/storage 1302 (intensity modulation characteristic storing process) before the inspection shown in FIG. 13 or the registering 1306 of VLmin and VHmax in response to the acquisition and storage, and thereby it is possible to not only suppress the explosive fracture of the large foreign matter with high accuracy, but also to obtain the maximum inspection beam power during normal inspection with high accuracy. Hence, it is possible to realize the improvement in the inspection sensitivity.

The present invention is not limited to the examples described above, and includes various modification examples. For example, the examples are described in detail for easy understanding of the present invention, and the present invention is not necessarily limited to inclusion of the entire configurations described above.

In addition, control wires or information wires are illustrated when the wires are considered to be necessary for description, and all of the control wires or the information wires are not necessarily illustrated for a product. Actually, almost all of the configurations may be considered to be connected to each other.

REFERENCE SIGNS LIST

1: wafer
2: laser beam source
3: optical modulation element
4: polarization plate
5: beam splitter
6: mirror
7, 8: lens
9: sensor
10: detection circuit
11: data processing unit
12: driver circuit
13: beam power detecting means
14: stage
51: input circuit
52, 53: high-voltage generating circuit
54, 55: level shift circuit
56, 57, 58, 59: MOS drive circuit
60, 62: PMOS transistor
61, 63: NMOS transistor
64, 65: high-voltage generating circuit
100, 110: foreign matter inspection device
7000: semiconductor inspection device (optical inspection device)
7002: specimen
706: illumination optical system
800: light source
804: Pockels cell
805: half-wave plate (wave plate)
806: polarization beam splitter
807: static attenuator
808: Pockels cell control unit
809: half-wave plate control unit
812: power monitor
814: intensity modulation characteristic storage unit
1000: intensity modulation characteristics
1302: intensity modulation characteristic storing process
1305: wave plate angle adjusting process

The invention claimed is:

1. A semiconductor inspecting device comprising:
a stage for mounting a specimen;
an illumination optical system; and
a detection unit,
   wherein the illumination optical system further comprises
   a laser beam source irradiating a laser beam;
   an electro-optic element which changes a polarization state of the laser beam from the laser beam source based on a voltage applied to the electro-optic element;
   a wave plate which changes the polarization state of the laser beam through the electro-optic element according to an angle of the wave plate; and
   a polarization beam splitter which diverge the laser beam through the wave plate with an intensity determined by the polarization state of the leaser beam,
   wherein, before inspecting the specimen, the angle of the wave plate is adjusted such that a lower intensity of the laser beam through the polarization beam splitter in state that a first voltage is applied to the electro-optic element, is lower than a higher intensity of the laser beam through the polarization beam splitter in a state that second voltage is applied to the electro-optic element, and
   wherein, during inspecting the specimen, the voltage applied to the electro-optic element is changed to the first voltage if a presence of foreign matter having a certain size is predicted.

2. A semiconductor inspecting device according to claim 1, wherein the wherein the electro-optic element is a Pockels cell.

3. A semiconductor inspecting device according to claim 1,
   wherein the wave plate is a half-wave plate, and
   wherein said lower intensity is equal or lower than 50% of said intensity.

* * * * *